US00PP22518P3

(12) United States Plant Patent
ten Have

(10) Patent No.: US PP22,518 P3
(45) Date of Patent: Feb. 21, 2012

(54) ***BEGONIA* PLANT NAMED 'HAVE02'**

(50) Latin Name: *Begonia elatior*
Varietal Denomination: Have02

(75) Inventor: Jos ten Have, Maasland (NL)

(73) Assignee: J and P TenHave B.V. (NL)

( * ) Notice: Subject to any disclaimer, the term of this patent is extended or adjusted under 35 U.S.C. 154(b) by 36 days.

(21) Appl. No.: 12/658,177

(22) Filed: Feb. 3, 2010

(65) Prior Publication Data

US 2011/0191922 P1 Aug. 4, 2011

(51) Int. Cl.
*A01H 5/00* (2006.01)

(52) U.S. Cl. ..... Plt./348

(58) Field of Classification Search ..... Plt./343, Plt./344, 348, 349
See application file for complete search history.

(56) References Cited

OTHER PUBLICATIONS

GTITM UPOVROM Citation for 'Pauline' as per NL PBR BGN0147; Jun. 6, 1988.*
GTITM UPOVROM Citation for 'Pauline' as per DK PBR 18308; Oct. 30, 1985.*
GTITM UPOVROM Citation for 'Pauline' as per 7947 (FR PBR 0147135); Aug 29, 1988.*

* cited by examiner

*Primary Examiner* — Kent L Bell

(57) ABSTRACT

A new and distinct *Begonia* cultivar named 'Have02' is disclosed, characterized by its unique light pink flower color and large foliage with an undulating margin. The new cultivar is a *Begonia,* typically suited for ornamental container use.

1 Drawing Sheet

Figure 1:
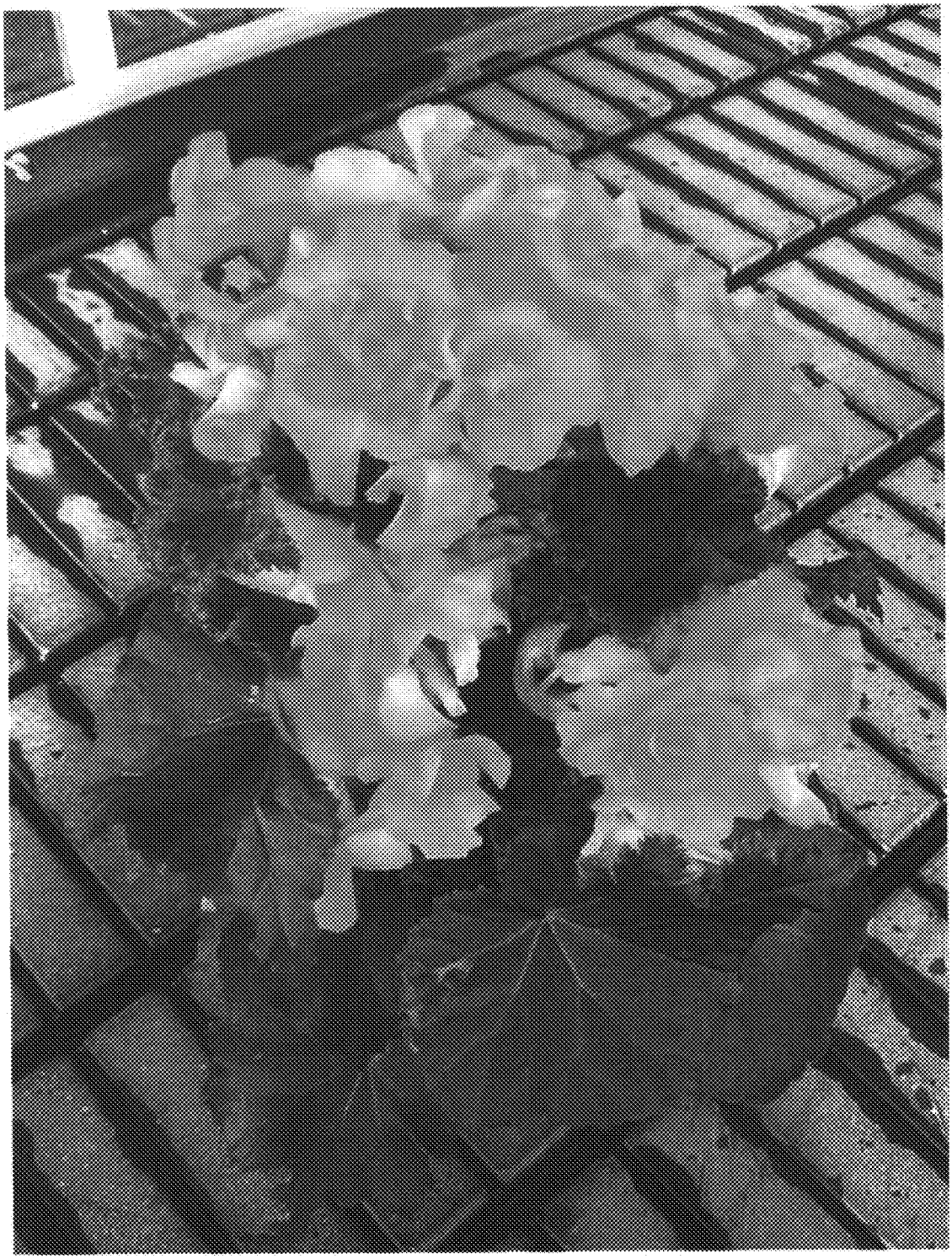

Latin name of the genus and species: *Begonia elatior.*
Variety denomination: 'Have02'.

BACKGROUND OF THE INVENTION

The new cultivar is the result of a chance discovery in an existing population of *Begonia elatior* plants. The new variety originated as a naturally occurring, whole plant mutation of the parent variety, the unpatented commercial variety, *Begonia elatior* 'Netja'. The new variety was discovered by the inventor in the Fall of 2007 at a commercial greenhouse in Maasland, the Netherlands.

After selecting and isolating the new cultivar, asexual reproduction of the new cultivar 'Have02' was first performed in the same commercial greenhouse by vegetative cuttings in the winter of 2008. 'Have02' has since produced several generations and has shown that the unique features of this cultivar are stable and reproduced true to type.

SUMMARY OF THE INVENTION

The cultivar 'Have02' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Have02'. These characteristics in combination distinguish 'Have02' as a new and distinct *Begonia* cultivar:

1. Large foliage, with an undulating margin.
2. Large flower size.
3. Distinctive light pink flower color.
4. Vigorous plants, growing to a large size.

PARENTAL COMPARISON

Plants of the new cultivar 'Have02' are similar to the parent 'Netja' in most horticultural characteristics. However, 'Have02' differs in producing larger foliage with an undulating margin and lighter pink flowers. Additionally, 'Have02' produces a larger overall plant size than 'Netja'.

COMMERCIAL COMPARISON

Plants of the new cultivar 'Have02' are best compared to the parent variety.

BRIEF DESCRIPTION OF THE PHOTOGRAPH

The accompanying photograph in FIG. 1 illustrates in full color a typical plant of 'Have02' grown in a greenhouse in Maasland, the Netherlands. This plant is approximately 10 weeks old, shown in a 10 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Have02' plants grown in a greenhouse in Maasland, the Netherlands during the Fall months. Temperatures ranged from 18° C. to 20° C. at night to 19° C. to 20° C. during the day. No artificial light, photoperiodic treatments or chemical treatments were given to the plants. Measurements and numerical values represent averages of typical plant types.

Botanical classification: *Begonia elatior* 'Have02'.

Age of the plant described: Approximately 10 weeks.

Container size of the plant described: 10 cm commercial container.

PROPAGATION

Time to initiate roots: Summer: 30 to 35 days at approximately 22° C. Winter: 35 to 40 days at approximately 22° C.

Root description: Fine, densely branched, non-fibrous, non-fleshy, colored near Grey-Brown N199A.

PLANT

Growth habit: Broad upright.
Pot size of plant described: 0.8 liter; 12 cm.
Height: 22.2 cm.
Plant spread: 26.3 cm.
Growth rate: Low to moderate.
Branching characteristics: Free branching.
Length of primary lateral branches: Average 8.4 cm.
Quantity of primary lateral branches: Average: 3.
Characteristics of primary lateral branches:
*Form.*—Rounded.
*Diameter.*—0.8 cm.
*Color.*—Near RHS Yellow-Green 146A and 146B, both colors present.
*Texture.*—Slightly glossy, very sparsely covered with short hairs, average length: 1 mm, colored near White NN155D.
*Strength.*—Moderate.
Internode length: 2.5 cm.

FOLIAGE

Leaf:
*Arrangement.*—Alternate.
*Quantity.*—Approximately 4 per branch.
*Average length.*—12.9 cm.
*Average width.*—9.9 cm.
*Shape of blade.*—Ovate.
*Apex.*—Acute.
*Base.*—Hastate, slightly overlapping.
*Margin.*—Biserrate, wavy.
*Texture of top surface.*—Smooth, velvety.
*Pubescence.*—Smooth, except for main veins of under side, which are very sparsely pubescent with short hairs, average length: 1 mm, colored near RHS white NN155D.
*Aspect.*—Leaf blade horizontal (=0°) to slightly pointed downward (average angle: 35°).
*Color.*—Young foliage upper side: Near RHS Yellow-Green 146A. Young foliage under side: A range of colors present between RHS Yellow-Green and 152A and 152B, all colors present. Mature foliage upper side: Near RHS N137D. Mature foliage under side: Near RHS Greyed-Green 191A.
*Venation.*—Type: Pinnate. Venation color upper side: RHS Yellow-Green 144A. Venation color under side: RHS Yellow-Green 147C.
*Petiole.*—Length: 6.5 cm. Diameter: 0.45 cm. Color: RHS Yellow-Green 146D. Texture: sparsely covered with short hairs, average length: 1.5 mm, colored near RHS white NN155D.
*Stipule description.*—Length: 1.6 cm. Diameter: 1.7 cm. Color: RHS Yellow-Green 145B. Texture: smooth, moderately glossy.

FLOWER

Natural flowering season: March until October.
Days to flowering from rooted cutting: 8 to 10 weeks.
Inflorescence and flower type and habit: Axillary and terminal clusters; individual flowers fully double.
Rate of flower opening: 5 to 10 days from bud to fully opened flower.
Flower longevity on plant: Approximately 28 days.
Persistent or self-cleaning: Self-cleaning.
Bud:
*Shape.*—Ovate to deltoid.
*Length.*—2.8 cm.
*Diameter.*—1.5 cm.
*Color.*—Near RHS Yellow-Green 145C.
Flower size:
*Diameter.*—6.2 cm.
*Depth.*—2.4 cm.
Tepals:
*Quantity.*—2.
*Arrangement.*—Opposite.
*Length.*—4.1 cm.
*Width.*—5.6 cm.
*Shape.*—Reniform.
*Apex.*—Broad rounded.
*Base.*—Truncate to reniform.
*Margin.*—Irregular crenulate, undulate.
*Texture, upper and lower surfaces.*—Both surfaces smooth, upper side slightly glossy, lower side moderately glossy.
*Color.*—When opening, upper surface: Near RHS Red 52D, base Yellow-Green 145D. When opening, lower surface: Near RHS Red 52D, base Yellow-Green 145D. Fully opened, upper surface: Near RHS Red 48C, edged 47B and 47C, both colors present, base Yellow-Green 145D. Fully opened, lower surface: Near RHS Red 49C and 49D, both colors present edged 47C, base Yellow-Green 145D.
Spurs: Not present.
Petaloids:
*Quantity.*—Average: 15.
*Length.*—2.5 cm.
*Width.*—3.0 cm.
*Shape (overall).*—Orbicular to reniform.
*Apex.*—Rounded.
*Base.*—Reniform.
*Margin.*—Irregular crenulate, undulate.
*Color.*—Near RHS Red 52C, base Yellow-Green 145D and lighter, both surfaces same color.
Peduncles:
*Length.*—2.2 cm.
*Diameter.*—0.25 cm.
*Angle.*—About 15° to the lateral branch.
*Strength.*—Weak.
*Texture.*—Slightly glossy, moderately covered with very short glandular hairs, average length: 0.3 mm, colored Yellow-Green 145D.
*Color.*—RHS Yellow-Green 145B.
Pedicels:
*Length.*—Approximately 0.8 cm.
*Diameter.*—Approximately 0.25 cm.

*Angle.*—About 35° to the peduncle attachment.
*Strength.*—Moderate.
*Texture.*—Slightly glossy.
*Color.*—RHS Yellow-Green 145B.
Bracts: Not observed to date.
Fragrance: No.

REPRODUCTIVE ORGANS

Stamens: No stamens observed.
Anthers: No anthers observed.
Pistil: No pistil observed.

OTHER CHARACTERISTICS

Seeds and fruits: No seeds/fruits observed.
Disease/pest resistance: Neither resistance nor susceptibility to normal pathogens and pests of *Begonia elatior* have been observed.
Temperature tolerance: Indoor plant, no frost tolerance.

What is claimed is:

1. A new and distinct cultivar of *Begonia elatior* plant named 'Have02' as herein illustrated and described.

* * * * *